United States Patent
Cohen

(10) Patent No.: US 6,313,181 B1
(45) Date of Patent: Nov. 6, 2001

(54) COSMETIC COMPOSITIONS CONTAINING OPTICAL BRIGHTENERS

(75) Inventor: Isaac D. Cohen, Brooklyn, NY (US)

(73) Assignee: Color Access, Inc., Melville, NY (US)

(*) Notice: Subject to any disclaimer, the term of this patent is extended or adjusted under 35 U.S.C. 154(b) by 0 days.

(21) Appl. No.: 09/320,153

(22) Filed: May 26, 1999

(51) Int. Cl.⁷ .................................................. A61K 7/02
(52) U.S. Cl. .................... 514/844; 424/401; 424/63; 424/69; 424/70.6; 424/70.7; 424/70.9; 424/70.11
(58) Field of Search ............................. 424/401, 63, 69, 424/70.6, 70.7, 70.9, 70.11; 514/844

(56) References Cited

U.S. PATENT DOCUMENTS

| | | |
|---|---|---|
| 5,143,723 | 9/1992 | Calvo et al. . |
| 5,324,506 | 6/1994 | Calvo et al. . |
| 5,626,839 | 5/2001 | Sclaes-Medeiros .................... 424/59 |
| 5,635,109 | 6/1997 | Otsuka . |
| 5,755,998 | 5/1998 | Yamazaki . |
| 5,830,446 | 11/1998 | Berthiaume et al. . |

FOREIGN PATENT DOCUMENTS

| | | | |
|---|---|---|---|
| 0 541 669 | 5/1993 | (EP) . | |
| 0 370 470 | 5/1997 | (EP) . | |
| 249 | 4/1967 | (FR) . | |
| 2773470 | 7/1999 | (FR) | ................................ A61K/7/04 |
| 62-277316 | 12/1987 | (JP) . | |
| 2060978 | 3/1990 | (JP) . | |
| 3250075 | 11/1991 | (JP) . | |
| WO 9606602 | 3/1996 | (WO) . | |

OTHER PUBLICATIONS

Michael J. Fellner, M.D., "Green Autofluorescence in Human Epidermal Cells" Arch Dermatol—vol. 112, pp. 667–670, (May 1976).

Haishan Zeng, et al., "Spectroscopic and Microscopic Characteristics of Human Skin Autofluorescence Emission", Photochemistry and Photobiology: vol. 61, No. 6, pp. 639–645, (1995).

David J. Leffell, M.D., et al., "In Vivo Fluorescence of Human Skin: A Potential Marker of Photoaging", Arch Dermatol—vol. 124, pp. 1514–1518 (Oct. 1998).

International Cosmetic Ingredient Dictionary and Handbook, 7th Edition 1997, vol. 2, Published by The Cosmetic, Toiletry, and Fragrance Association, Editors John A. Wenninger, et al., CTFA, pp. 1628–1630, and copy of book cover.

Sumita Optical Glass, Inc., 4–7-25 Harigaya, Urawa, Saitama, Japan, "New Active Fluorescence Glass—LUMILASS–R7/G9/B"—4 Pages—(Jul. 1, 1997).

*Primary Examiner*—Michael A. Williamson
(74) *Attorney, Agent, or Firm*—Kenyon & Kenyon

(57) ABSTRACT

The invention relates to cosmetic composition comprising a fluorescent-effective amount of at least one fluorescent brightener, in combination with a cosmetically acceptable vehicle. The compositions of the invention can be used as color cosmetics and skin treatment products, to replenish the skin's natural fluorescent glow.

30 Claims, No Drawings

COSMETIC COMPOSITIONS CONTAINING OPTICAL BRIGHTENERS

FIELD OF THE INVENTION

The invention relates to cosmetic compositions and methods. More specifically, the invention relates to compositions and methods that replenish the skin's natural fluorescence.

BACKGROUND OF THE INVENTION

It has long been recognized that normal skin exhibits a substantial level of fluorescence(Fellner, Arch. Dermatol. 112: 667–670, 1976). The fluorescence apparently exists throughout the different layers of the skin, with the epidermis showing the weakest levels, the stratum corneum being slightly stronger, and the most intense emissions being found in the dermis and subcutaneous fat(Zeng, et al., Photochem. Photobiol. 61: 639–645, 1995). The level of epidermal fluorescence varies depending upon the color of the individual's skin, with darker skins showing a higher level of fluorescence than lighter skins. However, the fluorescence in the dermis is apparently related to elements common to all skin types: elastin and collagen. The spectra of living human skin is measurable over a wide excitation wavelength, with green being the dominant autofluorescence color.

With particular respect to the dermis, it well-known that the elements responsible for fluorescence are susceptible to substantial alteration in quality and quantity due to advancing age as well as UV exposure. It is widely accepted that these changes in elastin and collagen are at least partially, and probably predominantly, responsible for many of the external changes characteristic of aged skin, whether chrono- or photoaged. The external changes that are immediately identifiable as being associated with loss or alteration of these fibers include the readily defined features, such as lines, wrinkles, and skin atrophy; however, another common age-associated feature that is perhaps more difficult to characterize is familiar loss of luster, color and tone of mature or photodamaged skin.

Interestingly, the change in structure of collagen and elastin observed at least with respect to photoaging has been shown to be correlated with a decline in the intensity of fluorescence in the photoaged skin.(Leffell, et al. Arch. Dermatol. 124: 1514–1518, 1988). This change is also reflected in chronoaged skin, which in middle age begins to lose its green fluorescence, and in later years, loses its blue fluorescence. It is very likely that the decline in the vigorous "glow" common to young, healthy skin is related at least in part to the this observed loss of fluorescence. Nonetheless, cosmetics and skin care products have traditionally focused on the camouflaging of the most easily characterized signs of aging, such as wrinkles; there has been little effort to develop products which address the seemingly more intangible problem of renewing the glow of youth in the more mature individual's skin. The present invention now provides a solution to this problem.

SUMMARY OF THE INVENTION

The present invention relates to skin-toned or non-color cosmetic compositions for application to the skin comprising effective amounts of at least one fluorescent brightener, in combination with a cosmetically acceptable vehicle. The compositions, when applied to the skin, replenish the fluorescence that may have been lost due to chrono- or photoaging, while not conferring any readily discernible amount of color on the skin. The invention also relates to a method of imparting a glow to the skin comprising applying to the skin a skin-toned or non-color cosmetic composition comprising an effective amount of a fluorescent optical brightener. The compositions can also be used to reduce the appearance of dark circles and lines on the skin, as well as reduce the appearance of symptoms of chrono-and photoaging.

DETAILED DESCRIPTION OF THE INVENTION

Fluorescent brighteners, also referred to as optical brighteners or fluorescent whiteners, are compounds falling into a number of different chemical classes, but which share the properties of being colorless on a substrate in ordinary light, while exhibiting a colored fluorescence when exposed to UV light. Traditional optical brighteners are organic, largely aromatic or heterocyclic, and are characterized by the presence of an uninterrupted chain of conjugated double bonds; the number of double bonds varies depending upon substituents and the planarity of the fluorescent part of the molecule. The fluorescence of these compounds is normally in the blue-violet range, with an excess of brightener sometimes resulting is a bluish-green color. In addition to these organic compounds, however, there are also synthetic inorganic compounds, such as fluorescent glasses, that exhibit similar properties, i.e., that are colorless on a substrate, but show a colored fluorescence. The range of colors of the latter may be more varied than traditional optical brighteners, coming in blues, reds, or greens. The term "fluorescent brightener" or its synonyms, in the present specification and claims, is intended to encompass both types of fluorescent compounds.

The general use of fluorescent brighteners in various industries is in compensation for a yellowish cast on the substrate to which the brightener is applied. This is achieved by the brightener's absorbtion of invisible UV light and its conversion into visible blue and blue-violet light; this addition of blue-to-violet light to a substrate counteracts its yellowish appearance, which is the result of absorption of the blue-to-violet light by the substrate. The ultimate result is essentially a pure white, with no loss of light. One of the most common uses for fluorescent brighteners is in laundry detergent, where they aid in increasing the brightness of white fabrics. They have also found widespread use in the textile industry to counteract the normal yellowish color of many fibers, both natural and synthetic. The paper industry employs brighteners to whiten pulp and to enhance the surface whiteness of preformed sheets of paper.

The use of fluorescent materials in cosmetics is not unknown. There are a number of reported uses of fluorescent pigments or dyes in cosmetics, particularly in color cosmetics, principally to impart an additional dimension to the color(see, e.g., EP 370470, JP 2060978, JP 3250075, and EP 542669). In each of these cases, a fluorescent dye or pigment, such as D&C Orange No. 5, or ultramarine blue, typically constitutes the sole or primary colorant component of the cosmetic, and the color of the dye is visually prominent in the product. Fluorescent brighteners have also been disclosed, in U.S. Pat. No. 5,635,109, for use in cosmetics, for the purpose of intensifying color or shine imparted by a cosmetic composition, such as nail lacquer, lipstick or a hair cuticle coat.

In contrast to the uses of fluorescent materials of prior art, however, the present invention utilizes fluorescent brighteners in such a way as to confer a fluorescent glow to both the composition and to the skin when applied, but does not confer any visually distinct color to the skin. Also in contrast to the prior art use of fluorescent materials, the compositions in which the brighteners are used do not brightly color the skin, but rather are skin-toned to virtually colorless. In certain embodiments, particularly in the case in which the optical brightener is used in a non-color cosmetic, the composition as a whole will not confer any discernible color change to the skin. The fluorescent brighteners can be used in a color cosmetic intended to mimic the color of human skin, such as a foundation, a blush, or a self-tanner, or it can also be used in a non-color cosmetic, e.g., a skin care or transparent or translucent cosmetic which is intended to confer little or no color to the skin after application. The term "effective amount" as used in the specification and claims is that amount of a fluorescent brightener that will confer an observable fluorescence under UV light to the composition in which it is placed.

Any cosmetically acceptable fluorescent brightener may be employed in the compositions of the invention. The brighteners can be conveniently grouped according to their chemical class. Commonly used organic fluorescent brighteners include compounds selected from the group consisting of organic compounds that are derivatives of stilbene and 4,4'-diaminostilbene, e.g., bistriazinyl derivatives; derivatives of benzene and biphenyl, e.g., styryl derivatives; pyrazolines, bis(benzoxazol-2-yl) derivatives, coumarins, carbostyrils, naphthalimides, s-triazines, pyridotriazoles, and the like. A review of commonly used fluorescent brighteners is found in "Fluorescent Whitening Agents", Kirk-Othmer Encyclopedia of Chemical Technology, Fourth Edition, Volume 11, Wiley and Sons, 1994, the contents of which are incorporated herein by reference. The fluorescent material may also be an inorganic fluorescent glass, such as are described in U.S. Pat. Nos. 5,635,109, and 5,755,998, the contents of which are incorporated herein by reference. A wide variety of such compounds are available commercially from, for example, Keystone Aniline Corp. (Chicago, Ill.) Ciba Specialty Chemicals, (High Point, NC) and Sumita Optical Glass, Inc. (Saitama, Japan). In one embodiment, the brightener produces a green to bluish green fluorescence; these include, for example, a rare earth fluorescent glass, such as Lumilass G9(Sumita). In another embodiment, the material emits a blue fluorescence; examples of such compounds include a distyryl biphenyl derivative known as Tinopal CBS-X(Ciba), an oxazole known as Keyfluor White, and an inorganic fluorescent glass, Lumilass B(Sumita). Other fluorescence categories include red or orange, as represented, for example by Lumilass R7. In one preferred embodiment, the material is selected from those emitting blue or green fluorescence, or combinations thereof, so as to directly mimic the skin's natural fluorescent color. However, in another embodiment, the material's fluorescent color can be any one or a combination of colors, the selection being made for the purpose of enhancing, complementing, or counteracting a given skin tone color.

The amount of the brightener may be varied depending upon the intensity of the fluorescence, and can be from about 0.0001% to about 50%; more typically, however, the amount used will be between about 0.001% up to about 10%, preferably about 0.01% to about 8%, with about 0.05–5% being the most commonly employed amount. The brighteners can be incorporated into any kind of vehicle that is normally used for facial cosmetic compositions. For example, the brighteners can be added to solutions, colloidal dispersions, emulsions(oil-in-water or water-in-oil), suspensions, powders, creams, lotions, gels, foams, mousses, sprays and the like. Methodology for formulation of different vehicle types is well known in the art, and can be found for example in Remington's The Science and Practice of Pharmacy, 19th Edition, Volume II. In one embodiment, the brighteners are used in a skin-toned powder color cosmetic, such as a face powder or body powder, or a powder blush. In another embodiment, the brighteners can be used as part of a liquid, solid or semi-solid color cosmetic, such as a liquid, cream, gel, or stick-type foundation, concealer, or blush. The compositions of this type are not brightly colored, but rather mimic the skin's natural color, and thus permit the most natural, advantageous and recognizable replenishment of the skin's natural luster.

In the case of the use of the brighteners in a skin-toned color cosmetic, the brightener will confer substantially no color to the product. In a color cosmetic, the brightener will be typically combined with other pigments or dyes. The additional color components can be either organic or inorganic. Examples of useful inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide(white) and mixtures thereof. Other useful pigments are pearlants such as mica, bismuth oxychloride and treated micas, such as titanated micas and lecithin modified micas.

The organic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Polymeric colorants include nylon powder, polyethylene, and polyesters. The polyesters can include linear, thermoplastic, crystalline or amorphous materials produced using one or more diols and one or more dicarboxylic acids copolymerized with colorants. An exemplary list of cosmetically acceptable colorants can be found in the International Cosmetic Ingredient Dictionary and Handbook, 7th Edition, CTFA, 1997, pp. 1628–1630, the contents of which are incorporated herein by reference. In the color cosmetics of the present invention, colorants other than the fluorescent brightener will normally constitute from about 0.1% to about 30% by weight of the composition, the amounts varying depending upon the color desired.

Although not traditionally considered a color cosmetic, self-tanning compositions, which confer a tanned color to the skin without exposure to sunlight, can also benefit by the presence of one or more fluorescent brighteners. In such a case, the self-tanner, which is normally the compound dihydroxyacetone(DHA), or a combination of DHA and imidazole, is used in an amount of from about 1 to about 10%, in combination with the chosen fluorescent compound (s).

In an alternate embodiment, the brighteners are employed in a non-color cosmetic, such as a transparent or translucent product, or a skin treatment product. When used in a skin treatment product, the brighteners can be used alone as the primary component, for the purpose of evening or brightening skin tone, to disguise dark shadows, undereye circles, lines and wrinkles on the skin, or to counteract the effects of rosacea. Alternately, they can be used in a product combined with additional skin care treatment actives, such as those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, antiaging agents, antiwrinkle agents, antiasthmatic agents and bronchodilators, sunscreen agents, antihistamine agents, skin lightening agents, depigmenting agents, wound-healing agents, vitamins, corticosteroids, self-tanning agents, or hormones. The amount of active agent to be used in any given formulation is readily determined in accordance with its usual dosage.

The mode of application of the compositions of the invention will depend upon the final intended use. In a color cosmetic/makeup product, the brightener-containing composition will normally be applied on an as-needed basis, to the face, or optionally the body, as part of the user's daily makeup routine. As a non-color cosmetic or treatment product, the composition can be applied daily, with or without makeup, simply to replenish the skin's natural glow and to cause unadorned skin to appear healthier and younger. It may also be applied to particular trouble spots, such as dark undereye shadows, in order to brighten their appearance. Although the amount of product applied will also vary depending upon the final end use, and the appearance intended to be achieved, as a guideline to achieve an optimum glow, the product will normally be applied in an amount of about 0.1 $\mu g/cm^2$ to 2 $mg/cm^2$ of skin, The invention is further illustrated by the following non-limiting examples.

EXAMPLES

Example I

This example illustrates the preparation of liquid foundation containing an optical brightener.

| Material | Weight Percent |
| --- | --- |
| Bean tree oil | 25.30 |
| Isoeicosane | 11.00 |
| Microcrystalline wax | 5.00 |
| Isododecane/quaternium-18/propylene carbonate | 6.00 |
| Spherical silica | 14.00 |
| Polymethylmethacrylate | 14.50 |
| Propyl paraben | 0.20 |
| Polymethysilsesquioxane | 5.00 |
| talc | 7.75 |
| Bean tree oil | 5.50 |
| Red iron oxide | 0.30 |
| yellow iron oxide | 0.75 |
| black iron oxide | 0.20 |
| titanium dioxide | 4.00 |
| 2,2'-(2,5-thiophenediyl)bis(5-(1,1-dimethyl)-benzoxazole (Keyfluor White PL) | 0.50 |

What is claimed is:

1. A method of providing a glow to the skin which comprises applying to the skin a composition comprising a fluorescent-effective amount of at least one fluorescent brightener, in combination with a cosmetically acceptable vehicle wherein the composition as a whole will not confer any discernable color change to the skin.

2. The method of claim 1 in which the brightener is an organic compound selected from the group consisting of derivatives of stilbene and 4,4'-diaminostilbene; derivatives of benzene and biphenyl; pyrazolines, derivatives of bis (benzoxazol-2-yl), coumarins, carbostyrils, naphthalimides, s-triazines, and pyridotriazoles.

3. The method of claim 1 in which the brightener is an inorganic fluorescent glass.

4. The method of claim 1 in which the brightener shows a green or blue fluorescence.

5. The method of claim 1 in which the composition is a non-color cosmetic.

6. The method of claim 1 in which the composition is a color cosmetic.

7. The method of claim 6 in which the composition is a foundation, blush or facial powder.

8. The method of claim 1 in which the composition is a skin-toned color cosmetic composition for application to skin comprising a fluorescent-effective amount of a fluorescent brightener, in combination with a cosmetically acceptable vehicle and at least one colorant selected from the group consisting of inorganic pigments, natural colorants, synthetic organic monomeric colorants, and synthetic organic polymeric colorants, a self-tanner, and combinations thereof.

9. The method of claim 8 in which the composition comprises at least one inorganic pigment selected from the group consisting of iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide(white), and combinations thereof.

10. The method of claim 9 in which the composition comprises at least one iron oxide, titanium dioxide, or a combination thereof.

11. The method of claim 8 in which the composition is a foundation, blush, concealer or facial powder.

12. The method of claim 8 in which the composition comprises a self-tanner which is DHA.

13. A method of reducing the appearance of dark shadows or lines on the skin which comprises applying to the skin a composition comprising a fluorescent-effective amount of at least one fluorescent brightener, in combination with a cosmetically acceptable vehicle wherein the composition as a whole will not confer any discernable color change to the skin.

14. The method of claim 13 in which the brightener is an organic compound selected from the group consisting of derivatives of stilbene and 4,4'-diaminostilbene; derivatives of benzene and biphenyl; pyrazolines, derivatives of bis (benzoxazol-2-yl), coumarins, carbostyrils, naphthalimides, s-triazines, pyridotriazoles and inorganic fluorescent glasses.

15. The method of claim 13 in which the brightener shows a green or blue fluorescence.

16. The method of claim 13 in which the composition is a non-color cosmetic.

17. The method of claim 13 in which the composition is a color cosmetic.

18. The method of claim 13 in which the composition is a skin-toned color cosmetic composition for application to skin comprising a fluorescent-effective amount of a fluorescent brightener, in combination with a cosmetically acceptable vehicle and at least one colorant selected from the group consisting of inorganic pigments, natural colorants, synthetic organic monomeric colorants, and synthetic organic polymeric colorants, a self-tanner, and combinations thereof.

19. A method of improving the appearance of chrono- or photoaged skin which comprises applying to the skin a composition comprising a fluorescent-effective amount of at least one fluorescent brightener, in combination with a cosmetically acceptable vehicle wherein the composition as a whole will not confer any discernable color change to the skin.

20. The method of claim 19 in which the brightener is an organic compound selected from the group consisting of derivatives of stilbene and 4,4'-diaminostilbene; derivatives of benzene and biphenyl; pyrazolines, derivatives of bis(benzoxazol-2-yl), coumarins, carbostyrils, naphthalimides, s-triazines, pyridotriazoles and inorganic fluorescent glasses.

21. The method of claim 19 in which the brightener shows a green or blue fluorescence.

22. The method of claim 19 in which the composition is a non-color cosmetic.

23. The method of claim 19 in which the composition is a color cosmetic.

24. A method of reducing the appearance of symptoms of rosacea on the skin which comprises applying to the skin a composition a comprising a fluorescent-effective amount of at least one fluorescent brightener, in combination with a cosmetically acceptable vehicle wherein the composition as a whole will not confer any discernable color change to the skin.

25. The method of claim 24 in which the composition is a skin-toned color cosmetic composition for application to skin comprising a fluorescent-effective amount of a fluorescent brightener, in combination with a cosmetically acceptable vehicle and at least one colorant selected from the group consisting of inorganic pigments, natural colorants, synthetic organic monomeric colorants, and synthetic organic polymeric colorants, a self-tanner, and combinations thereof.

26. The method of claim 24 in which the brightener is an organic compound selected from the group consisting of derivatives of stilbene and 4,4'-diaminostilbene; derivatives of benzene and biphenyl; pyrazolines, derivatives of bis(benzoxazol-2-yl), coumarins, carbostyrils, naphthalimides, s-triazines, pyridotriazoles and an inorganic fluorescent glass.

27. The method of claim 24 in which the brightener shows a green or blue fluorescence.

28. The method of claim 24 in which the composition is a non-color cosmetic.

29. The method of claim 24 in which the composition is a color cosmetic.

30. The method of claim 24 in which the composition is a skin-toned color cosmetic composition for application to skin comprising a fluorescent-effective amount of a fluorescent brightener, in combination with a cosmetically acceptable vehicle and at least one colorant selected from the group consisting of inorganic pigments, natural colorants, synthetic organic monomeric colorants, and synthetic organic polymeric colorants, a self-tanner, and combinations thereof.

* * * * *